(12) United States Patent
Zhang et al.

(10) Patent No.: US 8,658,842 B2
(45) Date of Patent: Feb. 25, 2014

(54) PROCESS FOR PRODUCING ETHYLENE GLYCOL CATALYZED BY IONIC LIQUID

(75) Inventors: Suojiang Zhang, Beijing (CN); Jian Sun, Beijing (CN); Weiguo Cheng, Beijing (CN); Jinquan Wang, Beijing (CN); Jianxin Zhang, Beijing (CN); Zengzeng Fu, Beijing (CN); Xiangping Zhang, Beijing (CN)

(73) Assignee: Institute of Process Engineering, Chinese Academy of Sciences (CN)

( * ) Notice: Subject to any disclaimer, the term of this patent is extended or adjusted under 35 U.S.C. 154(b) by 0 days.

(21) Appl. No.: 13/520,008

(22) PCT Filed: Jun. 7, 2010

(86) PCT No.: PCT/CN2010/000800
§ 371 (c)(1),
(2), (4) Date: Aug. 31, 2012

(87) PCT Pub. No.: WO2011/153656
PCT Pub. Date: Dec. 15, 2011

(65) Prior Publication Data
US 2013/0072727 A1   Mar. 21, 2013

(51) Int. Cl.
*C07C 29/09* (2006.01)

(52) U.S. Cl.
USPC ........................................................ 568/867

(58) Field of Classification Search
USPC ........................................................ 568/867
See application file for complete search history.

(56) References Cited

U.S. PATENT DOCUMENTS

| 2,667,497 A | 1/1954 | Cline |
| 2,773,070 A | 12/1956 | Lichtenwalter |

FOREIGN PATENT DOCUMENTS

| CN | 1161320 | 10/1997 |
| CN | 1308046 | 8/2001 |
| CN | 1415416 | 5/2003 |
| CN | 1416952 | 5/2003 |
| CN | 200310121060.0 | 6/2005 |
| CN | 1926125 | 3/2007 |
| CN | 1978415 | 6/2007 |
| CN | 101265253 | 9/2008 |
| CN | 101456792 | 6/2009 |
| GB | 2378701 | 2/2003 |
| JP | 57183784 | 11/1982 |
| JP | 58126884 | 7/1983 |
| JP | 3120270 | 5/1991 |
| JP | 7206847 | 8/1995 |
| JP | 2000143563 | 5/2001 |
| WO | 99/31033 | 6/1999 |

OTHER PUBLICATIONS

Paddock, Robert L. and SonBinh T. Nguyen, Chemical CO2 Fixation: Cr(III) Salen Complexes as Highly Efficient Catalysts for the Coupling of CO2 and Epoxides, J. Am. Chem. Soc. 123:11498-11499, 2001.
Shen, Yu-Mei et al., Chemical Fixation of Carbon Dioxide Catalyzed by Binaphthyldiamino Zn, Cu, and Co Salen-Type Complexes, J. Org. Chem. 68:1559-1562, 2003.
Doskocil, Eric J., Effects of Water and Alkali Modifications on ETS-10 for the Cycloaddition of CO2 to Propylene Oxide, J. Phys. Chem. B., 2005, 109, 2315-2320.
Xiao, Lin-Fei et al., Supported Basic Ionic Liquid: Highly Effective Catalyst for the Synthesis of 1,2-Propylene Glycol from Hydrolysis of Propylene Carbonate, J. Mo. Catal.A:ChemB, 2008, 279(2):230-234.
Peng, Jiajian and Deng, Youquan, Formation of Propylene Carbonate Catalyzed by Room Temperature Ionic Liquids, Chinese Journal of Catalysis, Nov. 2001, vol. 22, No. 6.
Wang, Yao-hong et al., Synthesis of Ethylene Glycol via Hydrolysis of Ethylene Carbonate Catalyzed by Immobilized Ionic Liquid, China Academic Journal Electronic Publishing House, Oct. 2009, vol. 9, No. 5.

*Primary Examiner* — Elvis O Price
(74) *Attorney, Agent, or Firm* — Barry L. Davison; Davis Wright Tremaine LLP

(57) ABSTRACT

Disclosed is a process for producing ethylene glycol catalyzed by an ionic liquid, characterized in that the process includes the following three steps: (a) a carbonylation step of ethylene oxide and $CO_2$ catalyzed by an ionic liquid composite catalyst comprising a hydroxyl functionalized ionic liquid and an alkali metal salt under an aqueous condition to produce ethylene carbonate and ethylene glycol; (b) a hydrolysis step of reacting the reaction solution containing ethylene carbonate and the ionic liquid composite catalyst obtained in step (a) with water to produce ethylene glycol; (c) a purification step of dehydrating and refining ethylene glycol from the aqueous solution containing ethylene glycol and the catalyst produced in step (b). The present process has the following advantages: the catalyst has high activity, high suitability, and good stability, the reaction condition is wild, the conversion of ethylene oxide is high, the selectivity of ethylene glycol is high, and the process is simple.

17 Claims, 1 Drawing Sheet

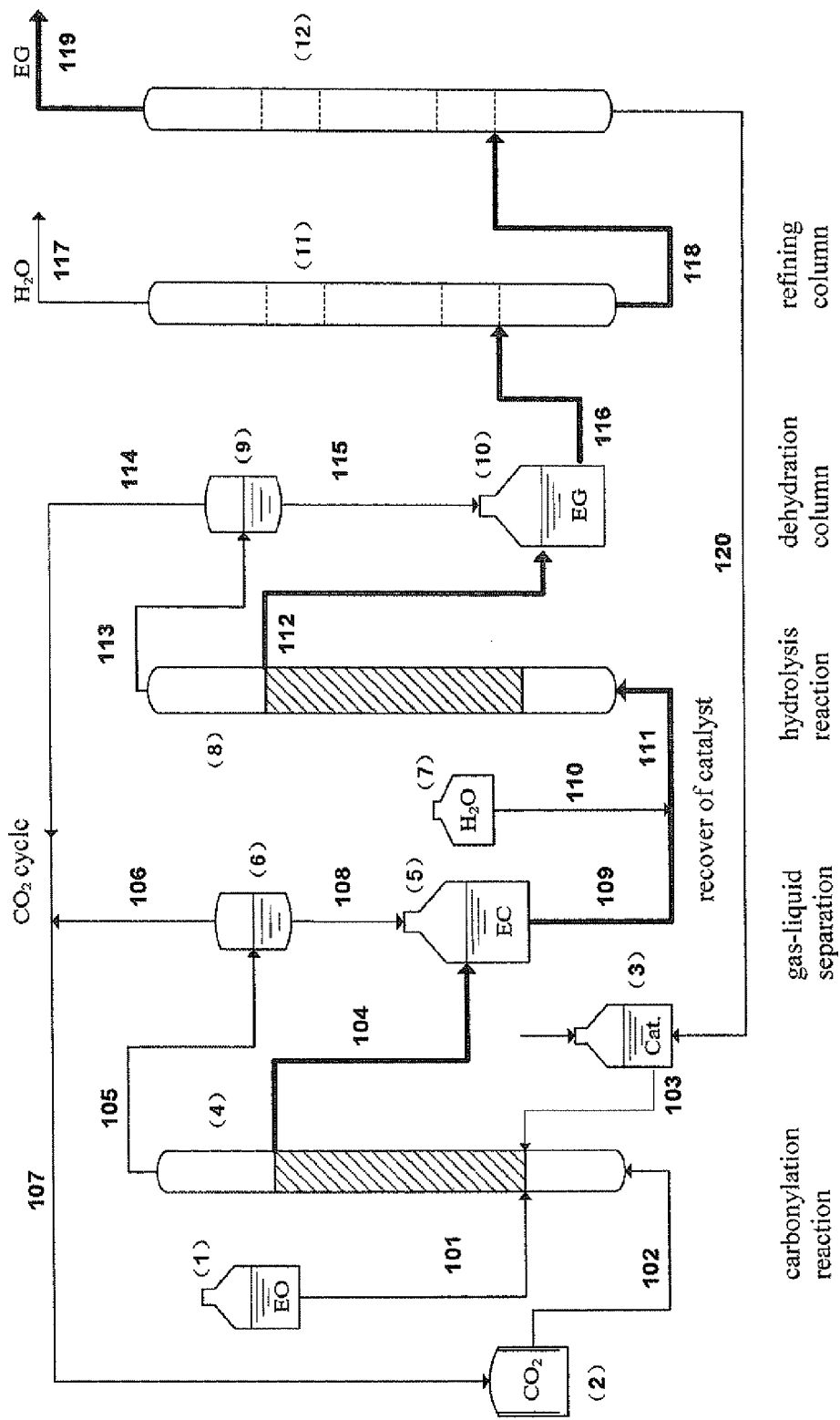

PROCESS FOR PRODUCING ETHYLENE GLYCOL CATALYZED BY IONIC LIQUID

TECHNICAL FIELD

The present invention relates to a process for producing ethylene glycol, particularly relates to a novel process for producing ethylene glycol from ethylene oxide based on the catalysis of an ionic liquid.

BACKGROUND ART

Ethylene glycol (EG) is one of important industrial base materials, which can be used to manufacture products like polyester fiber, antifreeze, unsaturated polyester resin, non-ionic surfactant, ethanolamine, explosive, and so on. Traditional EG production employs ethylene oxide (EO) direct hydration process (FIG. 1), but this process has many disadvantages of high water ratio (molar ratio of $H_2O$ to EO is up to 22:1), high energy consumption, poor selectivity of ethylene glycol (<89%), and so on.

Reaction Formula 1: ethylene oxide direct hydration process for producing ethylene glycol

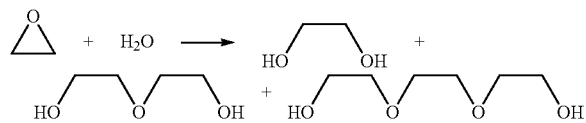

Recently, various new EG production technologies are successively developed, in which the representative ones are the catalytic hydration process (WO9931033A1) and ethylene carbonate process. Comparing with the direct hydration process, the water ratio in the catalytic hydration process is 3-10, and the selectivity of EG is less than 96%. The disadvantages of the hydration process are the low activity and the stability of the catalysts. The process for producing ethylene glycol via ethylene carbonate (Reaction Formula 2) is a process in which EO and $CO_2$ as raw materials are firstly subjected to a carbonylation reaction for synthesizing ethylene carbonate (EC) and followed by hydrolyzing EC to produce EG. Comparing this process with the direct hydration and the catalytic hydration processes, it has the advantages such as moderate reaction conditions, low water ratio ($H_2O$:EO=1.5:1 to 1.1:1), high EG selectivity (>99%), and low energy consumption. Famous international companies such as DOW, Texaco, Halcon-SD, Nippon Shokubai and Japan-Mitsubishi have already carried on the corresponding investigations. This process represents the development direction of ethylene glycol production.

Reaction Formula 2: ethylene carbonate process for producing ethylene glycol

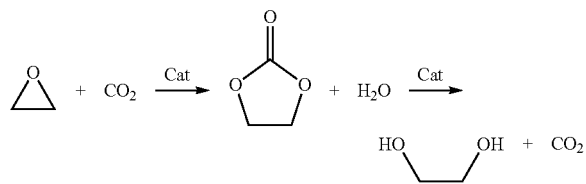

Because of the flammability, the explosibility, and the toxicity of EO, high efficient conversion of EO to produce EC have become the essential reaction of the EC process. At present the catalysts for producing EC, which have already been reported include homogeneous and heterogeneous types. Among them, the examples of the homogeneous catalysts are halides of alkaline earth metals (U.S. Pat. No. 2,667, 497, CN1926125A), transition metal complexes or quadridentate Schiff's alkali metal complexes (CN1416952, CN1415416), organic base (such as DMF and DBAP) (*J. Org. Chem.* 2003, 68, 1559), organic tin, germanium or tellurium compounds (JP57-183784), ionic liquids such as quaternary ammonium salts (such as tetrabutylammonium bromide, tetrabutylammonium chloride or tetrabutylammonium iodide) (U.S. Pat. No. 2,773,070), imidazolium salts (such as 1-butyl-3-methylimidazolium bromide, 1-ethyl-3-methylimidazolium bromide) (CN200310121060.0), quaternary phosphonium salts (such as tetrabutyl phosphonium iodide, triphenylmethyl phosphonium iodide and triphenylbenzyl phosphonium chloride) (CN1308046A, CN1161320A, JP58-126884, JP2000143563A). As for the heterogeneous catalysts, examples include solid alkalis (such as $MgO$—$Al_2O_3$) (*J. Am. Chem. Soc.* 2001, 123, 11498, CN101265253), molecular sieve (*J. Phys. Chem. B* 2005, 109, 2315-2320), anion exchange resin containing quaternary ammonium salts as exchanging groups (JP3-120270), and heteropolyacids based on tungsten oxides or molybdenum oxides and the salts thereof (JP7-206847), and so on.

Catalysts for EC hydrolysis which have been reported include homogeneous imidazolium acidic salts (such as [bmim]$HSO_4$ and [bmim]$H_2PO_4$) (CN1978415A), and supported basic imidazolium salts (such as PS-[bmim]OH and PS-[bmim]$HCO_3$) (CN101456792, *J. Mol. Cats. A: Chem.* 2008, 279(2): 230-234).

For these catalytic systems, more or less, there are problems such as poor catalyst activity, poor stability, severe reaction conditions, strong toxic organic solvent to be used and high catalyst cost. Development of the two step catalysts, which are cheap, high efficient, simple composition and environmental friendship, is urgently desired. On the other hand, in the current EC process, the carbonylation catalyst and the hydrolysis catalyst are generally used separately, because of the catalysts for these two steps are hard to be compatible. Such traditional technology directly results in complex catalyst separation, which leads to the corresponding complex separation process, high energy consumption, as well as influences the quality of EG product.

DISCLOSURE OF THE INVENTION

In view of the above problems, the present invention intends to provide a process for producing EG, in which a composite catalyst suitably used for carbonylation reaction and hydrolysis reaction at the same time is employed, so that the energy saving process for synthesis of EC and EG with high efficiency can be developed.

In order to achieve the above object, the present invention relates to a process for producing EG catalyzed by an ionic liquid composite catalyst, characterized in that the process includes the following three steps: (a) a carbonylation step of reacting EO and $CO_2$ in the presence of an ionic liquid composite catalyst under an aqueous condition to form an aqueous solution containing EC, the ionic liquid composite catalyst used being consisted of a hydroxyl functionalized ionic liquid and an alkali metal salt; (b) a hydrolysis step of reacting the reaction solution containing EC and the ionic liquid composite catalyst obtained in Step (a) with water to produce an aqueous solution containing EG; (c) a purification step of collecting and recovering EG from the aqueous solution containing EG produced in step (b). By the present invention, it is intended to use ionic liquid composite catalyst for the production of EG with a high efficiency and high selectivity at mild condition.

The general reaction formulae of the present invention are:

Reaction Formula 3: technical route of producing ethylene glycol by catalytic ethylene carbonate hydrolysis process

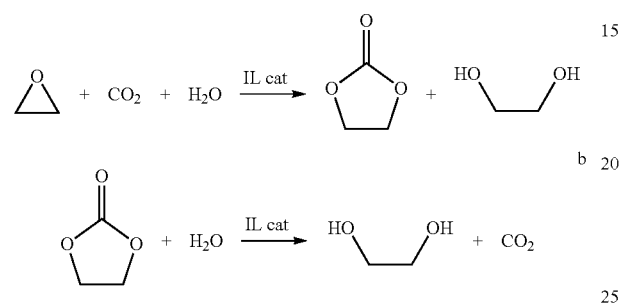

The ionic liquid composite catalyst used in the present invention is composed of the hydroxyl functionalized ionic liquid and the alkali metal salt. The hydroxyl functionalized ionic liquid refers to the ionic liquid with a hydroxyl alkyl group on the cation of the ionic liquid (for example, $N^+$, $P^+$), wherein the alkylene group acting as the linking group between the hydroxyl and the atom with positive charge may contain 2-10 carbon atoms. The hydroxyl functionalized ionic liquid includes a quaternary ammonium ionic liquid having a hydroxyl alkyl group and a quaternary phosphonium ionic liquid having a hydroxyl alkyl group, and the representative structural formulae thereof are as following:

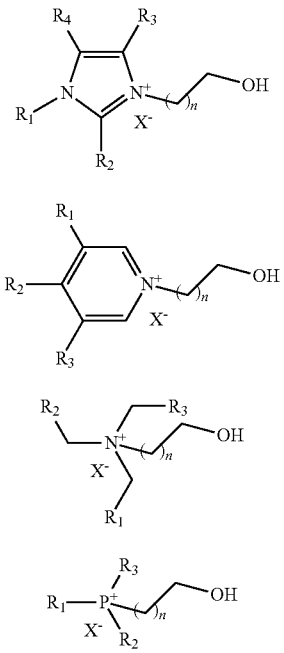

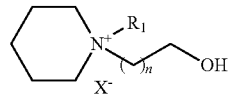

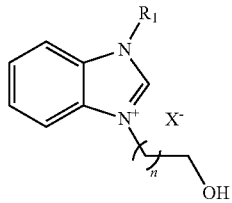

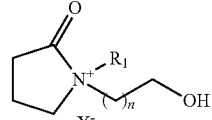

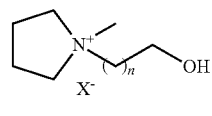

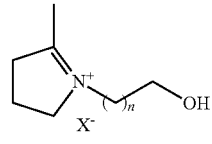

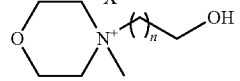

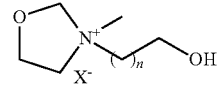

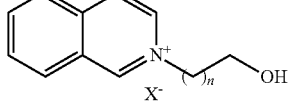

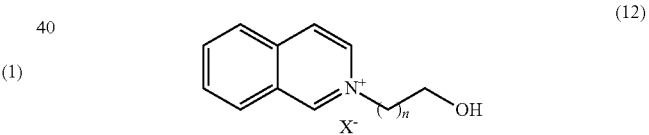

In the above structures, n=1-9; each of $R_1$, $R_2$, $R_3$, and $R_4$ is hydrogen or a substituent group selected from an alkane, an alkene, a cyclane, an arene, a halogenated alkane and a heterocyclic hydrocarbon with a carbon atom number of 1-20; X is an anion of the hydroxyl ionic liquid, which is selected from $Cl^-$, $Br^-$, and $I^-$.

The alkane in the present invention includes a C1-C14 alkane, preferably a C1-C19 alkane. The representative example of the alkene is allyl. The representative example of the cyclone is cyclohexyl. The arene includes phenyl, benzyl, tolyl, and so on. The halogenated alkane includes a halogenated C1-C4 alkane, and so on. The heterocyclic hydrocarbon includes such as imidazole, pyrrole, furan and thiophene.

The following structures of ionic liquid are used to illustrate the present invention, but the present invention is not limited to the following examples. Without deviating from the spirit of the present invention, all varied embodiments are included in the scope of the present invention.

Among the hydroxyl ionic liquids satisfying the above requirements, those of imidazolium-type (1) may be: 1-(2-hydroxyethyl)-3-methylimidazolium bromide, 1-(3-hydroxypropyl)-3-methylimidazolium bromide,
1-(4-hydroxybutyl)-3-methylimidazolium bromide,
1-(6-hydroxyhexyl)-3-methylimidazolium bromide,
1-(7-hydroxyheptyl)-3-methylimidazolium bromide,
1-(10-hydroxydecyl)-3-methylimidazolium bromide,
1-(2-hydroxyethyl)-3-bromoethane imidazolium bromide,
1-(2-hydroxyethyl)-3-[1-(2-hydroxyethyl)-3-ethylimidazolium]imidazolium bromide,
1-(4-hydroxybutyl)-3-benzylimidazolium bromide;
1-(2-hydroxyethyl)-3-methylimidazolium iodide,
1-(3-hydroxypropyl)-3-methylimidazolium iodide,
1-(4-hydroxybutyl)-3-methylimidazolium iodide,
1-(6-hydroxyhexyl)-3-methylimidazolium iodide,
1-(7-hydroxyheptyl)-3-methylimidazolium iodide,
1-(10-hydroxydecyl)-3-methylimidazolium iodide;
1-(4-hydroxybutyl)-3-methylimidazolium chloride,
1-(6-hydroxyhexyl)-3-methylimidazolium chloride,
1-(8-hydroxyoctyl)-3-methylimidazolium chloride, and
1-(9-hydroxynonyl)-3-methylimidazolium chloride.
  Those of pyridium-type (2) may be:
N-(3-hydroxypropyl)pyridium bromide,
N-(8-hydroxyoctyl)-4-methylpyridium bromide,
N-(8-hydroxyoctyl)-3-methylpyridium bromide,
N-(10-hydroxydecyl)-3-methylpyridium bromide;
N-(2-hydroxyethyl)pyridium iodide,
N-(3-hydroxypropyl)pyridium iodide,
N-(2-hydroxyethyl)-4-methylpyridium iodide;
N-(2-hydroxyethyl)pyridium chloride,
N-(8-hydroxyoctyl)-4-methylpyridium chloride,
N-(8-hydroxyoctyl)-3-methylpyridium chloride, and
N-(2-hydroxyethyl)-2-chloro-5-chloromethylpyridium chloride.
  Those of quaternary ammonium-type (3) may be:
1-(2-hydroxyethyl)-tributylammonium bromide,
1-(3-hydroxypropyl)-tributylammonium bromide,
1-(2-hydroxyethyl)-triethylammonium bromide,
1-(3-hydroxypropyl)-triethylammonium bromide,
1-(2-hydroxyethyl)-trihexylammonium bromide,
1-(6-hydroxyhexyl)-trihexylammonium bromide,
1-(7-hydroxyheptyl)-triheptylammonium bromide,
1-(10-hydroxydecyl)-tridecylammonium bromide;
1-(2-hydroxyethyl)-tributylammonium iodide,
1-(3-hydroxypropyl)-tributylammonium iodide,
1-(2-hydroxyethyl)-triethylammonium iodide,
1-(3-hydroxypropyl)-triethylammonium iodide,
1-(2-hydroxyethyl)-trihexylammonium iodide,
1-(6-hydroxyhexyl)-tribenzylammonium iodide,
1-(6-hydroxyhexyl)-trihexylammonium iodide,
1-(7-hydroxyheptyl)-triheptylammonium iodide,
1-(10-hydroxydecyl)-tridecylammonium iodide;
1-(2-hydroxyethyl)-tributylammonium chloride,
1-(3-hydroxypropyl)-tributylammonium chloride,
1-(2-hydroxyethyl)-triethylarnmonium chloride,
1-(3-hydroxypropyl)-triethylammonium chloride,
1-(2-hydroxyethyl)-trihexylammonium chloride,
1-(6-hydroxyhexyl)-trihexylammonium chloride,
1-(7-hydroxyheptyl)-triheptylammonium chloride, and
1-(10-hydroxydecyl)-tridecylammonium chloride.
  Those of quaternary phosphonium-type (4) may be:
1-(2-hydroxyethyl)-triphenylphosphonium bromide,
1-(3-hydroxypropyl)-triphenylphosphonium bromide,
1-(10-hydroxydecyl)-tributylphosphonium bromide,
1-(2-hydroxyethyl)-tripyrrolylphosphonium bromide,
1-(2-hydroxyethyl)-tricyclohexylphosphonium bromide,
1-(3-hydroxypropyl)-tri(2-furyl)phosphonium bromide,
1-(3-hydroxypropyl)-tri(2-thienyl)phosphonium bromide,
1-(3-hydroxypropyl)-tri(2-tolyl)phosphonium bromide;

1-(2-hydroxyethyl)-triphenylphosphonium iodide;
1-(2-hydroxyethyl)-triphenylphosphonium iodide,
1-(2-hydroxyethyl)-tricyclohexylphosphonium iodide,
1-(2-hydroxyethyl)-tripyrrolylphosphonium iodide,
1-(10-hydroxydecyl)-triphenylphosphonium iodide;
1-(2-hydroxyethyl)-triphenylphosphonium chloride,
1-(2-hydroxyethyl)-tripyrrolylphosphonium chloride,
1-(2-hydroxyethyl)-tricyclohexylphosphonium chloride,
1-(2-hydroxyethyl)-tetradecylphosphonium chloride, and
1-(10-hydroxydecyl)-tributylphosphonium chloride.
  Those of piperidinium-type (5) may be:
N-methyl-N-(2-hydroxyethyl)piperidinium bromide,
N-methyl-N-(6-hydroxyhexyl)piperidinium bromide,
N-ethyl-N-(7-hydroxyheptyl)piperidinium bromide,
N-propyl-N-(8-hydroxyoctyl)piperidinium bromide,
N-allyl-N-(2-hydroxyethy)piperidinium bromide,
N-methyl-N-(10-hydroxydecyl)piperidinium bromide;
N-methyl-N-(2-hydroxyethyl)piperidinium iodide,
N-methyl-N-(6-hydroxyhexyl)piperidinium iodide,
N-ethyl-N-(7-hydroxyheptyl)piperidinium iodide,
N-propyl-N-(8-hydroxyoctyl)piperidinium iodide,
N-allyl-N-(2-hydroxyethyl)piperidinium iodide,
N-methyl-N-(10-hydroxydecyl)piperidinium iodide;
N-methyl-N-(2-hydroxyethyl)piperidinium chloride,
N-methyl-N-(6-hydroxyhexyl)piperidinium chloride,
N-ethyl-N-(7-hydroxyheptyl)piperidinium chloride,
N-propyl-N-(8-hydroxyoctyl)piperidinium chloride,
N-allyl-N-(2-hydroxyethyl)piperidinium chloride, and
N-methyl-N-(10-hydroxydecyl)piperidinium chloride.
  Those of benzimidazolium-type (6) may be:
1-(2-hydroxyethyl)-3-methylbenzimidazolium bromide,
1-(3-hydroxypropyl)-3-ethylbenzimidazolium bromide,
1-(4-hydroxybutyl)-3-butylbenzimidazolium bromide,
1-(6-hydroxyhexyl)-3-ethylbenzimidazolium bromide,
1-(7-hydroxyheptyl)-3-ethylbenzimidazolium bromide,
1-(10-hydroxydecyl)-3-methylbenzimidazolium bromide,
1-(2-hydroxyethyl)-3-bromoethane benzimidazolium bromide,
1-(4-hydroxybutyl)-3-benzylbenzimidazolium bromide;
1-(2-hydroxyethyl)-3-methylbenzimidazolium iodide,
1-(3-hydroxypropyl)-3-ethylbenzimidazolium iodide,
1-(4-hydroxybutyl)-3-methylbenzimidazolium iodide,
1-(6-hydroxyhexyl)-3-methylbenzimidazolium iodide,
1-(7-hydroxyheptyl)-3-methylbenzimidazolium iodide,
1-(10-hydroxydecyl)-3-methylbenzimidazolium iodide;
1-(2-hydroxyethyl)-3-methylbenzimidazolium chloride,
1-(4-hydroxybutyl)-3-methylbenzimidazolium chloride,
1-(6-hydroxyhexyl)-3-ethylbenzimidazolium chloride,
1-(8-hydroxyoctyl)-3-methylbenzimidazolium chloride, and
1-(9-hydroxynonyl)-3-methylbenzimidazolium chloride.
  Those of pyrrolidonium-type (7) may be:
N-methyl-(2-hydroxyethyl)pyrrolidonium bromide,
N-methyl-(7-hydroxyheptyl)pyrrolidonium bromide,
N-ethyl-(10-hydroxydecyl)pyrrolidonium bromide;
N-methyl-(2-hydroxyethyl)pyrrolidonium iodide,
N-methyl-(7-hydroxyheptyl)pyrrolidonium iodide,
N-ethyl-(10-hydroxydecyl)pyrrolidonium iodide;
N-methyl-(2-hydroxyethyl)pyrrolidonium chloride,
N-methyl-(7-hydroxyheptyl)pyrrolidonium chloride, and
N-ethyl-(10-hydroxydecyl)pyrrolidonium chloride.
  Those of N-methylpyrrolium-type (8) may be:
N-methyl-N-(2-hydroxyethyl)pyrrolium bromide,
N-methyl-N-(7-hydroxyheptyl)pyrrolium bromide,
N-methyl-N-(10-hydroxydecyl)pyrrolium bromide;
N-methyl-N-(2-hydroxyethyl)pyrrolium iodide,
N-methyl-N-(7-hydroxyheptyl)pyrrolium iodide,
N-methyl-N-(10-hydroxydecyl)pyrrolium iodide;

N-methyl-N-(2-hydroxyethyl)pyrrolium chloride,
N-methyl-N-(7-hydroxyheptyl)pyrrolium chloride, and
N-methyl-N-(10-hydroxydecyl)pyrrolium chloride.

Those of 2-methylpyrrolinium-type (9) may be:
N-(2-hydroxyethyl)-2-methylpyrrolinium bromide,
N-(4-hydroxybutyl)-2-methylpyrrolinium bromide,
N-(7-hydroxyheptyl)-2-methylpyrrolinium bromide,
N-(10-hydroxydecyl)-2-methylpyrrolinium bromide;
N-(2-hydroxyethyl)-2-methylpyrrolinium iodide,
N-(4-hydroxybutyl)-2-methylpyrrolinium iodide,
N-(6-hydroxyhexyl)-2-methylpyrrolinium iodide,
N-(7-hydroxyheptyl)-2-methylpyrrolinium iodide,
N-(10-hydroxydecyl)-2-methylpyrrolinium iodide;
N-(2-hydroxyethyl)-2-methylpyrrolinium chloride,
N-(6-hydroxyhexyl)-2-methylpyrrolinium chloride,
N-(7-hydroxyheptyl)-2-methylpyrrolinium chloride, and
N-(10-hydroxydecyl)-2-methylpyrrolinium chloride.

Those of morpholinium-type (10) may be:
N-(2-hydroxyethyl)morpholinium bromide,
N-(4-hydroxybutyl)morpholinium bromide,
N-(7-hydroxyheptyl)morpholinium bromide,
N-(10-hydroxydecyl)morpholinium bromide;
N-(2-hydroxyethyl)morpholinium iodide,
N-(4-hydroxybutyl)morpholinium iodide,
N-(6-hydroxyhexyl)morpholinium iodide,
N-(7-hydroxyheptyl)morpholinium iodide,
N-(10-hydroxydecyl)morpholinium iodide;
N-(2-hydroxyethyl)morpholinium chloride,
N-(6-hydroxyhexyl)morpholinium chloride,
N-(8-hydroxyoctyl)morpholinium chloride,
N-(7-hydroxyheptyl)morpholinium chloride, and
N-(10-hydroxydecyl)morpholinium chloride.

Those of oxazolium-type (11) may be:
N-(2-hydroxyethyl)oxazolium bromide,
N-(3-hydroxypropyl)oxazolium bromide,
N-(6-hydroxyhexyl)oxazolium bromide,
N-(10-hydroxydecyl)oxazolium bromide;
N-(2-hydroxyethyl)oxazolium iodide,
N-(4-hydroxybutyl)oxazolium iodide,
N-(7-hydroxyheptyl)oxazolium iodide,
N-(8-hydroxyoctyl)oxazolium iodide,
N-(10-hydroxydecyl)oxazolium iodide;
N-(2-hydroxyethyl)oxazolium chloride,
N-(6-hydroxyhexyl)oxazolium chloride,
N-(8-hydroxyoctyl)oxazolium chloride,
N-(7-hydroxyheptyl)oxazolium chloride, and
N-(10-hydroxydecyl)oxazolium chloride.

Those of isoquinolinium-type (12) may be:
1-(2-hydroxyethylisoquinolinium bromide,
1-(3-hydroxypropyl)isoquinolinium bromide,
1-(4-hydroxybutyl)isoquinolinium bromide
1-(6-hydroxyhexyl)isoquinolinium bromide,
1-(7-hydroxyheptyl)isoquinolinium bromide,
1-(10-hydroxydecyl)isoquinolinium bromide;
1-(2-hydroxyethyl)isoquinolinium iodide,
1-(3-hydroxypropyl)isoquinolinium iodide,
1-(4-hydroxybutyl)isoquinolinium iodide,
1-(6-hydroxyhexyl)isoquinolinium iodide,
1-(7-hydroxyheptyl)isoquinolinium iodide,
1-(10-hydroxydecyl)isoquinolinium iodide;
1-(2-hydroxyethyl)isoquinolinium chloride,
1-(3-hydroxypropyl)isoquinolinium chloride,
1-(4-hydroxybutyl)isoquinolinium chloride,
1-(6-hydroxyhexyl)isoquinolinium chloride,
1-(7-hydroxyheptyl)isoquinolinium chloride, and
1-(10-hydroxydecyl)isoquinolinium chloride.

On the other hand, the alkali metal salt combined with the hydroxyl functionalized ionic liquid is selected from the group consisting of such as alkoxides, hydroxides, halides, phosphates, carbonates, sulfates, bicarbonates, and hydrophosphates of alkali metals Li, Na, and K.

In the ionic liquid composite catalyst of the present invention, in view of the effects on the catalyst activity of the composite catalyst and on the selectivity of reaction products in the both steps of carbonylation reaction and hydrolysis reaction, the mass ratio of the metal salt and the hydroxyl functionalized ionic liquid is 1:1-1:20, preferably 1:2-1:10. Under the above ratio, the ionic liquid composite catalyst exhibits high activity in both the carbonylation reaction and the hydrolysis reaction, the reaction selectivity is very high, and the separation and treatment of catalyst between respective reaction steps are not necessary.

The reaction conditions used in the present invention are further characterized by the following items.

(1) The reaction is carried out under an aqueous condition. In the carbonylation reaction, the water content in the system comprises 0.1-50.0%, by mass, preferably 2.0-50.0% by mass of the initial reaction solution. The addition of water helps to improve EO conversion in the carbonylation reaction, and as the amount of water increases, the amount of EG produced by the carbonylation reaction is increased correspondingly. The water in the carbonylation reaction system may come from industrial water-containing EO, and also may come from the solution of the composite catalyst.

(2) The composite catalyst is used in a form of solution. The composite catalyst solution may be only composed of the hydroxyl functionalized ionic liquid and the alkali metal salt, or may further contain a solvent. As for the solvent used for composite catalyst solution, there is no particular limitation, but in view of the solubility of the composite catalyst therein, the effect on the reaction, the cost, and so on, the solvent used is preferably EG, water, or the combination thereof. In the case of employing EG as the solvent, the content of EG comprises 0.4-50.0% of the total mass of the initial reaction solution. The addition of EG has significant effect on the reaction selectivity in the carbonylation reaction, that is, by the synergistic effect of hydroxyl groups, EG may also improve the carbonylation reaction catalyzed by the ionic liquid, but at the same time, it may react with EO to produce a given amount of diethylene glycol (DEG) byproduct, therefore the adding amount of EG is needed to be controlled.

(3) The other reaction conditions are characterized in that, in step (a), the molar ratio of the reacted EO and the reacted $CO_2$ is between 1:1-1:10, the catalyst amount is lower than 10.0 mol % of the moles of EO, the required reaction pressure is 0.5-5 MPa, the temperature is 50-180° C., and the reaction time is 0.1-5 h; in step (b), EC is mixed with 1-5 times molar equivalent of water, the required reaction pressure is 0.3-1.5 MPa, the temperature is 80-180° C., and the reaction time is 0.5-4 h; in the purification step (c), the aqueous solution containing EG is firstly subjected to a dehydration column for removing water, at a dehydration temperature of 100-190° C. and a pressure of 1-20 kPa; and then it is sent into a refining column to conduct EG refining, at a refining temperature of 100-190° C. and a pressure of 1-20 kPa.

In the process for producing EG of the present invention, the hydroxyl functionalized ionic liquid and the alkali metal salt have good compatibility, and the composite catalyst consisted of them has the advantages such as high activity, good stability, mild reaction conditions, and environmental friendship. Furthermore, the separation and treatment of catalyst are not required between respective steps, therefore the process is dramatically simplified, and cost saving.

DESCRIPTION OF FIGURES

FIG. 1 is a schematic diagram of the process flow of the present invention.

SPECIFIC MODE FOR CARRYING OUT THE INVENTION

The following examples are to illustrate the present invention, but the present invention is not limited to the following examples. Without deviating from the spirit of the present invention, all varied embodiments are included in the scope of the present invention.

Example 1

The carbonylation step (a): three streams of reaction materials, i.e. water-containing EO, $CO_2$, and catalyst solution, were fed from the storage tanks (1)-(3) to a bubble bed reactor (4), through pipes 101, 102, 103 respectively, in a mass flow ratio of 3:1:6; wherein the percentage of water contained in EO was about 7%, the purity of $CO_2$ was 99%; the catalyst solution was composed of EG and the composite ionic liquid catalyst, with a mass ratio of about 5:1, the catalyst was composed of 1-(2-hydroxyethyl)-3-methylimidazolium bromide and potassium carbonate in a mass ratio of 6:1. The reaction temperature was controlled to 125° C. by a temperature controller, and the reaction pressure was controlled to 2.5 MPa by a pressure valve. After reacting for 1.0 h, liquid phase products were sent through pipe 104 into EC storage tank (5), and gas phase products were sent through pipe 105 into gas-liquid separator (6) to separate $CO_2$ which did not completely react, and then through pipe 108 into the EC storage tank. Taking a sample to analysis the composition of the liquid phase, it was analyzed that the conversion of EO was close to 100%, the content of EO in the solution was lower than the detectability of chromatogram (10 ppm or less), the selectivity of EC was 90%, and the selectivity of EG was 10%. Heavy components, DEG and TEG were not detected. The solution obtained in step (a) was then fed to the EC hydrolysis step.

The hydrolysis step (b): the solution containing EC and EG obtained in step (a) was sent through pipe 109, wherein it was mixed with water from storage tank (7), then passed through pipe 111 and entered hydrolysis tubular reactor (8). The molar ratio of water and EC was 1.5:1, the reaction temperature was controlled to 140° C., and the reaction pressure was controlled to 0.4 MPa by a pressure valve. After reacting for 1.0 h, liquid phase products were sent through pipe 112 into EG storage tank (10), and gas phase products were sent through pipe 113 into gas-liquid separator (9) to separate out $CO_2$, and then through pipe 115 into storage tank (10). By the gas chromatography analysis of reaction solution, the results were that the conversion of EC was 100%, and the selectivity of EG was 100%. The solution obtained in (b) was then fed to EG purifying step.

The purifying step (c): firstly, the aqueous solution containing EG was subjected to dehydration column (11) to remove water, where the dehydration temperature was 150° C., and the pressure was 10 kPa; and then it was sent through pipe 118 into refining column (12) to conduct the EG refining, where the refining temperature was 160° C., and the pressure was 10 kPa. The EG product having a purity of 99.8% or more was obtained, which was sent from the head of the column through pipe 119 into EG storage tank; EG and catalyst remained in the column kettle were separated out and sent through pipe 120 for recycling.

Example 2

The carbonylation step (a) was conducted in the bubble bed reactor. Three streams of reaction materials were pure EO, catalyst solution, and $CO_2$, respectively, in a mass flow ratio was 2:1:4 (mass ratio). Wherein the purity of EO used was 99%, the purity of $CO_2$ was 99%. The catalyst solution was composed of water, EG and composite ionic liquid catalyst, with a mass ratio of about 1:4:1; the catalyst was composed of 1-(2-hydroxyethyl)-tributylammonium bromide and potassium phosphate, in a mass ratio of 4:1. The temperature was raised slowly to 130° C. under the control of the temperature controller. The reaction pressure was controlled to 2.0 MPa by the pressure valve. After reacting for 1.0 h, a sample was taken to conduct chromatographic analysis. The sample mainly contained EG, EC, and a small amount of water. The conversion of EO was close to 100%, and the content of EO in the solution was lower than the detectability of gas chromatogram (10 ppm or below). The selectivity of EC was 88%, the selectivity of EG was 12%. There were only trace amount of heavy components such as DEG and TEG.

The hydrolysis step (b) was same as example 1, expect that the reaction temperature was controlled to 150° C., and the reaction pressure was controlled to 0.6 MPa. The results of the gas chromatography analysis of the reaction products were that the conversion of EC was 100%, and the selectivity of EG was 100%.

The purifying step (c): the dehydration temperature was 140° C., and the pressure was 10 kPa; the refining temperature was 160° C., and the pressure was 10 kPa. The EG product having the purity of 99.8% or more was obtained; EG and catalyst remained in the column kettle were separated out for the next recycling reaction.

Example 3

The carbonylation step (a) was conducted in the bubble bed reactor. Three streams of reaction materials were water-contained EO, catalyst solution, and $CO_2$, respectively, and the feeding ratio was 3:0.5:9 (mass ratio), wherein the water content of EO used was 9%, and the purity of $CO_2$ was 99%. The catalyst solution was composed of EG and composite ionic liquid catalyst in a ratio of 4:1, wherein the catalyst was composed of 1-(2-hydroxyethyl)-triphenyl phosphonium chloride and potassium iodide in a ratio of 3:1. The reaction conditions were controlled so that the temperature was 140° C., the pressure was 3.5 MPa, and the reaction time was 2.5 h. After the reaction, it was measured that the conversion of EO was close to 100%, the selectivity of EC was 68%, and the selectivity of EG was 32%. After $CO_2$ contained reaction liquid was subjected to the gas-liquid separation, the obtained solution was fed to the hydrolysis step.

The hydrolysis step (b) and step (c) were the same as (b) and (c) in example 1.

Example 4

The reaction materials and step (c) were same as those in example 1, and other differences were as follows.

(1) The hydroxyl ionic liquid catalyst was 1-(3-hydroxypropyl)-3-ethylimidazolium bromide, combined with potassium biphosphate in a mass ratio of 2:1.

(2) In step (a), the reaction temperature was controlled to 110° C. by the temperature controller, and the reaction pressure was controlled to 3.0 MPa. After reacting for 1.0 h, the conversion of EO was 99.8%, the selectivity of EC was 60.5%, the selectivity of EG was 39.4%, and the selectivity of the other by-products was 0.1%.

(3) In step (b), the molar ratio of EC and water was 1:2, the reaction kettle temperature was controlled to 130° C., and the reaction pressure was controlled to 0.5 MPa. After reacting for 1.0 h, the composition of the liquid was measured, and it was calculated that the conversion of EC was 100%, and the selectivity of EG was 100%.

Example 5

The reaction materials were same as example 1, and other differences were as follows.

(1) The hydroxyl ionic liquid catalyst was 1-(3-hydroxypropyl)-pyridium iodide, formulated with sodium bicarbonate in a mass ratio of 8:1.

(2) In step (a), the reaction temperature was controlled to 100° C. by the temperature controller, and the reaction pressure was controlled to 2.0 MPa. After reacting for 1.5 h, the conversion of EO was 99.9%, the selectivity of EC was 81.5%, and the selectivity of EG was 18.5%.

(3) In step (b), the molar ratio of EC and water was 1:3, the reaction kettle temperature was controlled to 120° C., and the reaction pressure was controlled to 0.5 MPa. After reacting for 2.0 h, the composition of the liquid was measured, and it was calculated that the conversion of EC was 100%, and the selectivity of EG was 100%.

(4) In step (c), the conditions of dehydration operation were as follows. The dehydration temperature was 160° C., and the pressure was 15 kPa. The refining temperature was 170° C., and the pressure was 10 kPa. The EG product having a purity of 99.8% or more was obtained.

Example 6

This example was similar to example 1, except that the catalyst was composed of 1-(2-hydroxyethyl)-3-methylimidazolium bromide and sodium methylate in a mass ratio of 7:1. It was measured that the conversion of EO in step (a) was 99.9%. Among the products, the selectivity of EC was 85%, and the selectivity of EG was 15%. Steps (b) and (c) were same as those in example 1.

Example 7

The catalyst in example 1 was reused after 3 times of recycles. It was measured that the conversion of EO in Step (a) was close to 100%, the selectivity of EC was 89%, and the selectivity of EG was 11%. Heavy components, DEG and TEG were not detected.

In step (b), the conversion of EC was 100%, and the selectivity of EG was 100%.

The purity of the EG product obtained in Step (c) was 99.8% or more.

Example 8

The ionic liquid composite catalyst in example 1 was changed to 1-ethyl-3-methylimidazolium bromide and potassium carbonate. The reaction conditions were not changed. It was measured that, in step (a), the conversion of EO was only 92%, the selectivity of EC was 85%, and the selectivity of EG was 15%. Heavy components, DEG and TEG, were not detected. Step (b) was same as that in example 1, expect that the reaction time was 1.5 h; and step (c) was same as that in example 1.

Example 9

This example was similar to example 1, except that the catalyst was composed of 1-(7-hydroxyheptyl)-3-methylimidazolium bromide and sodium methylate in a mass ratio of 7:1. It was measured that, in step (a), the conversion of EO was 99%. Among the products, the selectivity of EC was 88%, and the selectivity of EG was 12%. Steps (b) and (c) were same as those in example 1.

Example 10

This example was similar to example 1, except that the catalyst was composed of N-(8-hydroxyoctyl)-4-methylpyridium bromide and potassium phosphate in a mass ratio of 10:1. It was measured that the conversion of EO in step (a) was 99.8%. Among the products, the selectivity of EC was 90%, and the selectivity of EG was 10%. Steps (b) and (c) were same as those in example 1.

Example 11

This example was similar to example 1, except that the composite catalyst was composed of N-propyl-N-(8-hydroxyoctyl)piperidinium iodide and potassium carbonate in a mass ratio of 10:1. In the case that the reaction conditions were not changed, it was obtained that the conversion of EO was 99.9%, the selectivity of EC was 94%, and the selectivity of EG was 6%.

In step (b), the conversion of EC was 100%, and the selectivity of EG was 100%.

The purity of the EG product obtained in step (c) was 99.8% or more.

Example 12

This example was similar to example 1, except that the composite catalyst was composed of 1-(2-hydroxyethyl)-3-methylbenzimidazolium chloride and potassium carbonate in a mass ratio of 8:1. In the case that the reaction conditions were not changed, it was obtained that the conversion of EO was 99.9%, the selectivity of EC was 92%, and the selectivity of EG was 8%.

In step (b), the conversion of EC was 100%, and the selectivity of EG was 100%.

The purity of the EG product obtained in step (c) was 99.8% or more.

Example 13

This example was similar to example 1, except that the water content of EO was 10%, the composite catalyst was composed of N-methyl-(7-hydroxyheptyl)pyrrolidonium iodide, potassium phosphate and potassium sulfate in a mass ratio of 6:0.5:0.5, the carbonylation reaction temperature was 130° C., and the reaction time was 50 min. In the case that the other reaction conditions were not changed, it was obtained that the conversion of EO was 99.8%, the selectivity of EC was 88%, and the selectivity of EG was 12%.

In step (b), the conversion of EC was 100%, and the selectivity of EG was 100%.

The purity of the EG product obtained in step (c) was 99.8% or more.

Example 14

This example was similar to example 1, except that the water content of EO was 10%, the composite catalyst was composed of N-methyl-N-(2-hydroxyethyl)pyrrolium bromide and potassium phosphate in a mass ratio of 7:1. In the case that the other reaction conditions were not changed, it was obtained that the conversion of EO was 99.8%, the selectivity of EC was 90%, and the selectivity of EG was 10%.

In step (b), the conversion of EC was 100%, and the selectivity of EG was 100%.

The purity of the EG product obtained in step (c) was 99.8% or more.

Example 15

This example was similar to example 1, except that the composite catalyst was composed of N-(7-hydroxyheptyl)-2-methylpyrrolinium iodide and potassium iodide in a mass ratio of 4:1. In the case that the other reaction conditions were not changed, it was obtained that the conversion of EO was 99.8%, the selectivity of EC was 96%, and the selectivity of EG was 4%.

In step (b), the hydrolysis reaction time was 2.5 h, and the conversion of EC was 100%, the selectivity of EG was 100%.

The purity of the EG product obtained in step (c) was 99.8% or more.

Example 16

This example was similar to example 1, except that the composite catalyst was composed of N-(8-hydroxyoctyl) morpholinium chloride and potassium chloride in a mass ratio of 6:1. In the case that the other reaction conditions were not changed, it was obtained that the conversion of EO was 99.7%, the selectivity of EC was 96%, and the selectivity of EG was 4%.

In step (b), the hydrolysis reaction time was 3 h, the reaction temperature was 150° C., the pressure was 0.5 MPa, the conversion of EC was 100%, and the selectivity of EG was 100%.

The purity of the EG product obtained in step (c) was 99.8% or more.

Example 17

This example was similar to example 1, except that the composite catalyst was composed of N-(10-hydroxydecyl) oxazolium iodide and potassium bromide in a mass ratio of 5:1, and the reaction time was 1.5 h. In the case that the other reaction conditions were not changed, it was obtained that the conversion of EO was 99.9%, the selectivity of EC was 95%, and the selectivity of EG was 5%.

In step (b), the hydrolysis reaction time was 2 h, the reaction temperature was 150° C., the pressure was 0.5 MPa, the conversion of EC was 100%, and the selectivity of EG was 100%.

The purity of the EG product obtained in step (c) was 99.8% or more.

Example 18

This example was similar to example 1, except that the composite catalyst was composed of 1-(7-hydroxyheptyl) isoquinolinium bromide and potassium carbonate in a mass ratio of 3:1. In the case that the other reaction conditions were not changed, it was obtained that the conversion of EO was 99.8%, the selectivity of EC was 86%, and the selectivity of EG was 14%.

In step (b), the conversion of EC was 100%, and the selectivity of EG was 100%.

The purity of the EG product obtained in step (c) was 99.8% or more.

Example 19

This example was used for comparing with example 3, except that the composite catalyst was composed of triphenylethylphosphonium chloride and potassium iodide, others were not changed. After the reaction it was measured that the conversion of EO was 91%, the selectivity of EC was 67%, the selectivity of EG was 31%, and the byproduct DEG was 2%. After $CO_2$ contained in the reaction liquid was subjected to gas-liquid separation, the obtained solution was fed to the hydrolysis Step.

The hydrolysis step (b) was same as that in example 3, except that the reaction time was 2 h, and step (c) was same as that in example 3.

Example 20

This example was used for comparing with example 1, and the differences were as follows:

The carbonylation step (a): the catalyst solution was composed of EG and 1-(2-hydroxyethyl)-3-methylimidazolium bromide in a mass ratio of about 5:1. The other conditions were not changed. To analyze the composition of the liquid phase, it was measured that the conversion of ED was close to 100%, the selectivity of EC was 93%, and the selectivity of EG was 7%. Heavy components, DEG and TEG, were not detected. The solution obtained in step (a) was then fed to the carbonic ester hydrolysis step.

The hydrolysis step (b): the solution containing EC, EG and hydroxyl ionic liquid catalyst obtained in step (a) was subjected to hydrolysis, others were not changed. It was measured that the conversion of EC was only 45%, and the selectivity of EG was 100%. The solution obtained in (b) was then fed to EG purifying step.

The purifying step (c) is different from step (c) in example 1, in that EC which was not completely reacted was contained in the solution used for purification. After the refining, the EG product having a purity of 99% was obtained. The components of the column kettle liquid were EG, EC, and the catalyst.

Example 21

This example was used for comparing with example 1, and the differences were as follows:

The carbonylation step (a): the catalyst solution was composed of EG and potassium carbonate in a mass ratio of about 35:1. The other conditions were not changed. To analyze the composition of the liquid phase, it was measured that the conversion of EO was only 10%, the selectivity of EC was 3%, the selectivity of EG was 89%, the selectivity of DEG was 7%, and the selectivity of TEG was 1%. After the separation of ethylene oxide which was not completely reacted in step (a), the solution obtained was then fed to the carbonic ester hydrolysis step.

The hydrolysis step (b): the solution containing EC, EG, DEG, TEG and potassium carbonate obtained in step (a) was subjected to the hydrolysis. The results were that the conversion of EC was 100%, and the selectivity of EG was 100%. The solution obtained in (b) was then fed to EG purifying step.

The purifying step (c): this step was same as that in example 1.

From the above results it can be seen that, in examples 1-7, 9-18 employing the ionic liquid composite catalyst of the present invention, the composite catalyst has high catalyst activity and good selectivity in both carbonylation and hydrolysis reactions. Comparing with the traditional ionic liquid without hydroxyl, the hydroxyl functionalized ionic liquid has significant better reaction performance (comparing example 1 with example 8, and example 3 with example 19), and therefore, the catalyst can be used for potentially industrial application. Based on the results in example 20 using ionic liquid catalyst alone and in example 21 using alkali metal salt catalyst alone, it can be seen that the activity of the catalyst in the EC hydrolysis step (example 20) or in the carbonylation step (example 21) was significantly lower than the ionic liquid composite catalyst.

In summary, in the process for producing EG of the present invention, the hydroxyl functionalized ionic liquid and the alkali metal salt have good compatibility. The composite catalyst consisted of them has high activity, which can efficiently catalyze the synthesis of EC and its hydrolysis to produce EG. Such composite catalyst has advantages of good catalyst stability, mild reaction conditions, and environmental friendship. Furthermore, the separation and treatment of catalyst were not required between respective steps, and the composite catalyst can be recycled, therefore the process was dramatically simplified, and was cost saving.

The invention claimed is:

1. A process for producing ethylene glycol catalyzed by a ionic liquid, characterized in that the process includes the following three steps:
   (a) a carbonylation step of ethylene oxide and $CO_2$ catalyzed by an ionic liquid composite catalyst comprising a hydroxyl functionalized ionic liquid and an alkali metal salt under an aqueous condition to produce ethylene carbonate and ethylene glycol, wherein the reaction formula is as follows:

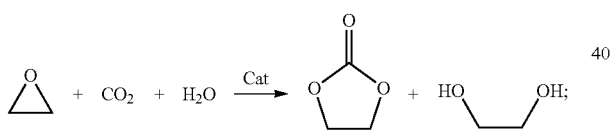

(b) a hydrolysis step of the reaction solution containing ethylene carbonate and the ionic liquid composite catalyst obtained in step (a) with water to produce ethylene glycol, wherein the reaction formula is as follows:

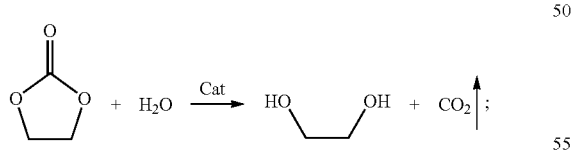

(c) a purification step of dehydrating and refining ethylene glycol from the aqueous solution containing ethylene glycol and the catalyst produced in step (b),
   wherein the hydroxyl functionalized ionic liquid represents an ionic liquid containing a hydroxyl alkyl group on its cation.

2. The process according to claim 1, characterized in that said hydroxyl functionalized ionic liquid is a quaternary ammonium type ionic liquid having a hydroxyl alkyl group or a quaternary phosphonium type ionic liquid having a hydroxyl alkyl group.

3. The process according to claim 1, characterized in that the alkylene group acting as a linking group between the hydroxyl group and the atom with positive charge in said hydroxyl functionalized ionic liquid contains 2-10 carbon atoms.

4. The process according to claim 1, characterized in that said hydroxyl functionalized ionic liquid is an ionic liquid represented by any one of the following structural formulae:

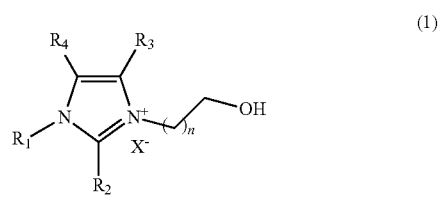

(1)

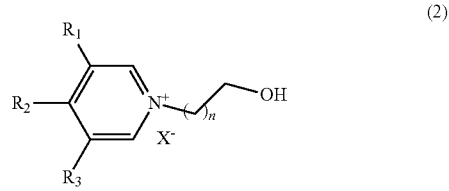

(2)

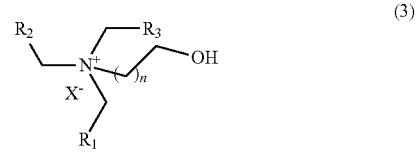

(3)

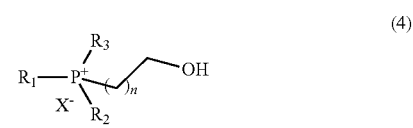

(4)

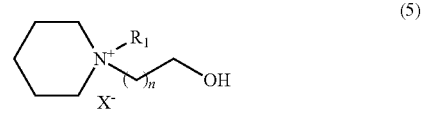

(5)

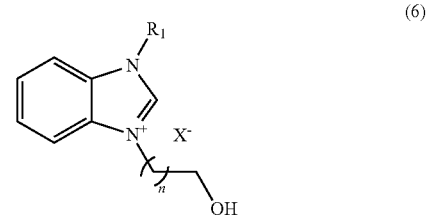

(6)

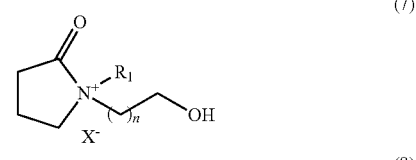

(7)

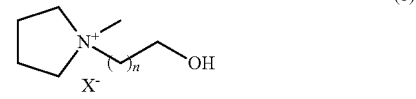

(8)

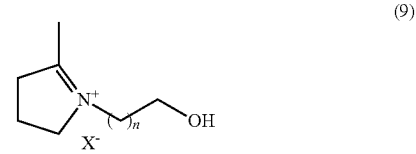

(9)

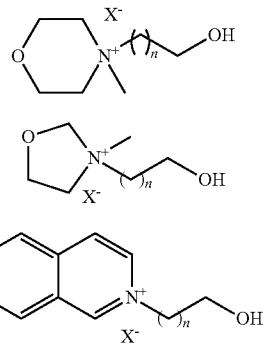

in the above structures, n=1-9; each of $R_1$, $R_2$, $R_3$, and $R_4$ is hydrogen or a substituent group selected from an alkane, an alkene, a cyclane, an arene, a halogenated alkane and a heterocyclic hydrocarbon with a carbon atom number of 1-20; X is an anion of the hydroxyl ionic liquid, which is selected from Cl, Br, and I.

5. The process according to claim 1, characterized in that the alkali metal salt is selected from the group consisting of alkoxides, hydroxides, halides, phosphates, carbonates, sulfates, bicarbonates, and hydrophosphates of the alkali metal Li, Na, and K.

6. The process according to claim 1, characterized in that the mass ratio of the alkali metal salt and the hydroxyl functionalized ionic liquid is 1:1-1:20.

7. The process according to claim 5, characterized in that the mass ratio of the alkali metal salt and the hydroxyl functionalized ionic liquid is 1:2-1:10.

8. The process according to claim 1, characterized in that the amount of the catalyst is lower than 10.0 mol % of the moles of ethylene oxide.

9. The process according to claim 1, characterized in that the water content of the system is 0.1-50.0% by mass of the initial reaction liquid.

10. The process according to claim 1, characterized in that the initial reaction system comprises ethylene glycol in a content of 0-50.0% by mass of the reaction liquid.

11. The process according to claim 1, characterized in that in Step (a) the molar ratio of reacted ethylene oxide and $CO_2$ is between 1:1-1:10.

12. The process according to claim 1, characterized in that in the Step (a) the required reaction pressure is 0.5-5 MPa, the temperature is 50-180° C., and the reaction time is 0.1-5 h.

13. The process according to claim 1, characterized in that in Step (b) ethylene carbonate and 1-5 times molar equivalents of water are mixed to carry out the hydrolysis reaction.

14. The process according to claim 1, characterized in that in the hydrolysis Step (b) the required reaction pressure is 0.3-1.5 MPa, the temperature is 80-180° C., and the reaction time is 0.5-4 h.

15. The process according to claim 1, characterized in that in the purification Step (c), firstly the aqueous solution containing ethylene glycol is subjected to a dehydration treatment through a dehydration column, at a dehydration temperature of 100-190° C. and a pressure of 1-20 kPa; and then it is fed to a refining column for refining ethylene glycol, at a refining temperature of 100-190° C. and a pressure of 1-20 kPa.

16. The process according to claim 1, characterized in that the hydrolysis Step (b) is carried out after the reaction solution containing ethylene carbonate and the ionic liquid composite catalyst produced in Step (a) is subjected to a gas-liquid separation.

17. The process according to claim 1, characterized by further comprising Step (d): after the purification Step (c), the catalyst is fed back to the Step (a) for recycling.

* * * * *